United States Patent [19]

Heasley

[11] 4,177,565
[45] Dec. 11, 1979

[54] PROXIMAL BOX JIG

[76] Inventor: John M. Heasley, 307 - 22nd St., NE., Cedar Rapids, Iowa 52402

[21] Appl. No.: 931,509

[22] Filed: Aug. 7, 1978

[51] Int. Cl.² ............................................. A61C 3/00
[52] U.S. Cl. .................................................. 433/75
[58] Field of Search ................................. 32/40 R, 67

[56] References Cited

U.S. PATENT DOCUMENTS

| | | | |
|---|---|---|---|
| 2,224,264 | 12/1940 | Jeanneret | 36/67 |
| 2,634,501 | 4/1953 | Linet | 32/67 |
| 2,675,615 | 4/1954 | Rosenberg | 32/67 |
| 3,011,259 | 12/1961 | Baum | 32/67 |
| 3,063,149 | 11/1962 | Suga | 32/67 |
| 3,073,561 | 1/1963 | Jermyn | 32/67 |
| 3,254,413 | 6/1966 | Suga | 32/67 |
| 3,839,797 | 10/1974 | Randolph | 32/67 |

*Primary Examiner*—Robert Peshock
*Attorney, Agent, or Firm*—Haven E. Simmons; James C. Nemmers

[57] ABSTRACT

A jig for the cutting of proximal boxes or outline forms in dentistry employs a guide table and paralleling arm. The guide table is located over the teeth by the clamping action of a pair of depending retentive arms which engage the embrasure area between adjacent teeth. The paralleling arm, which receives the dental burr, is swingable over the guide table and the latter and the arms in turn are provided with guide surfaces for determining the location and attitude of the buccal, lingual, axial and cervical walls of a proximal box.

10 Claims, 7 Drawing Figures

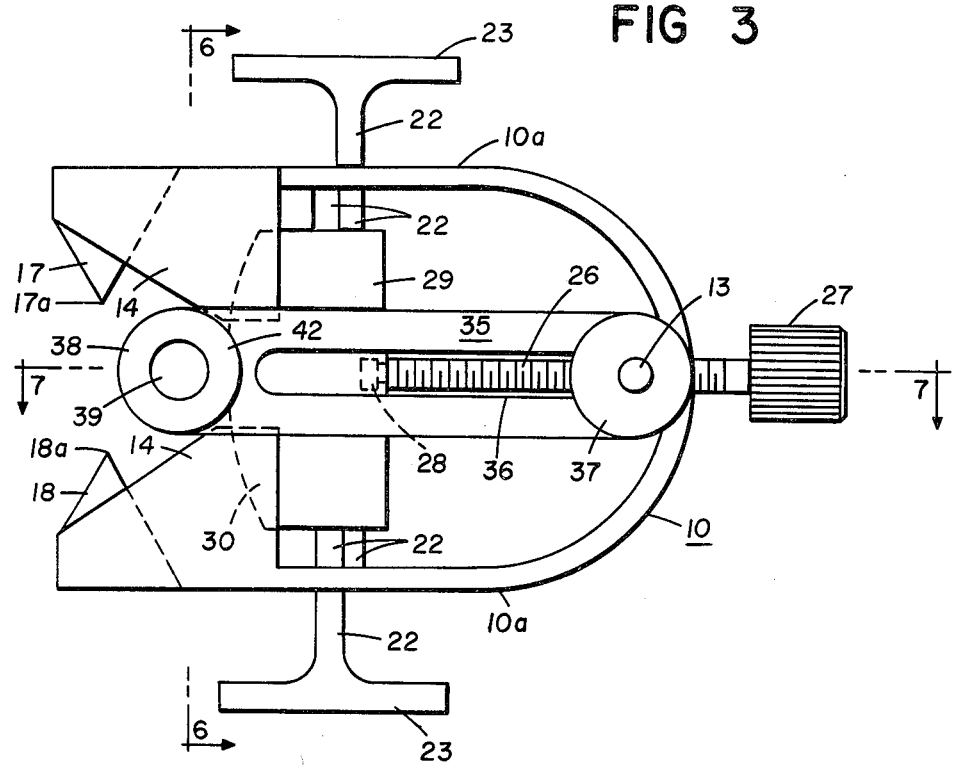
FIG 3
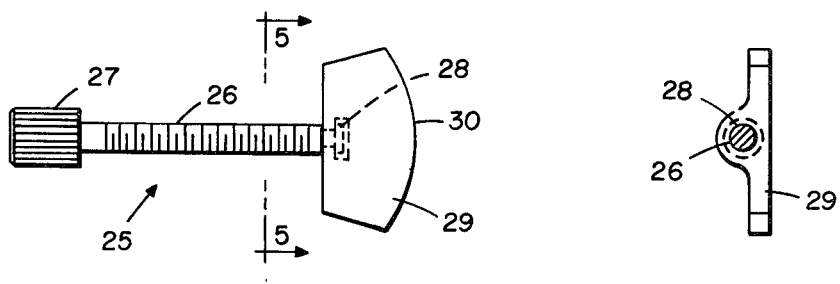
FIG 4
FIG 5

PROXIMAL BOX JIG

BACKGROUND OF THE INVENTION

Much dental work necessarily involves various kinds and amounts of tooth reduction. Examples, for instance, include the preparation of proximal boxes or outline forms for such materials as amalgam, cast or compacted gold, and sometimes composite restorative filling materials. Large carious lesions dictate the outline form of the cavity, but it is the small or moderate lesion on the proximal surface of the tooth that taxes the skill of the operator (the Class II lesion). Also requiring a great deal of skill on the part of the operator is the prepartion of two or more proximal boxes with a common path of insertion for the fabrication of the cast gold restoration. There is a large number of various jigs, guides, and templates which engage the teeth for dental work of assorted kinds, see for example, U.S. Pat. Nos. 2,224,264; 2,634,501; 2,675,615; 3,011,259; 3,063,149; 3,073,561; 3,254,413; and 3,839,797. Yet typically the practice is to cut proximal outline forms or boxes almost "free hand", so to speak, a laborious and time consuming operation and one which causes much stress on the part of the operator to achieve a consistently accurate result. Despite this fact and the profusion of existing jigs and templates, there is and has been nothing, so far as is known, directed specifically to all aspects of the preparation of proximal outline forms or boxes. This, therefore, is the primary object of the present invention.

SUMMARY OF THE INVENTION

The invention provides a template or jig basically in the nature of a guide table which overlies the tooth or teeth concerned. The guide table is formed by the legs of a U-shaped spring member whose outer ends are provided with a pair of right angled interproximal retentive arms in order to clamp the embrasure areas between adjacent teeth and thus hold the template in position and adjust it to proper proximal extensions and outline form. A paralleling arm is slidably pivoted to the end of the guide table remote from the retentive arms so that it is movable over the area of the guide table, one end of the paralleling arm carrying a guide for the dental burr. The dental burr is restrained from contacting the adjacent tooth by the paralleling arm in its maximum terminal position. Below the paralleling arm a horizontal stop or guide controls the location of the axial wall of the proximal box while a pair of opposite stops or guides on the spaced legs of the guide table controls the location of the buccal and lingual walls or extension of the box. A stop or guide on the paralleling arm controls the cervical extension or wall of the proximal box by limiting the depth of the cut of dental burr. The guides or stops are all in proper relation to the buccal, lingual and cervical walls of the box once the jig in turn is properly positioned by the retentive arms in the embrasure areas.

Once in position, the jig allows quick removal of proximal tooth structure, with accurate extensions into embrasure areas and formation of walls approaching 90° to the surface of the tooth while protecting the adjacent tooth from damage by the dental burr. This can be accomplished with greater ease and less stress to the operator during the course of the day than is the case when working "free hand" as is usually done. For small lesions, this amount of tooth removal will be sufficient except for minor refinement during the time of occlusal outline preparation. For slightly larger lesions additional removal of carious material may be necessary with a round burr or the preparation may require the manual extension of a wall or walls. As later explained, a slightly different form of the jig may be required for cast gold preparations vs. amalgam preparations owing to the differences in extensions and wall angulations. Use of different burrs (straight fissure vs. tapered fissure) with the device will produce convergence or parallelism vs. divergence of walls for materials of different physical properties.

In addition, the template can be quickly repositioned to a second proximal surface to prepare a second proximal box whose axial, buccal, and lingual walls share a common path of insertion with the first box. This is accomplished by using the paralleling arm as a reference for positioning of the jig with respect to the first box. All these features and advantages stem basically from the use of the interproximal embrasure areas to locate the jig, and thereby the position of the buccal, lingual and cervical walls of a box, together with the paralleling arm to guide the burr and as a reference device for adjacent boxes. The foregoing, as well as other features and advantages of the invention, will appear more clearly from the drawings and the more detailed description which follows.

BRIEF DESCRIPTION OF THE DRAWINGS

FIG. 3 is a top plan view taken along the lines 3—3 of FIG. 2.

FIG. 4 is a top plan view of the axial wall guide.

FIG. 5 is a sectional view taken along the line 5—5 of FIG. 4.

DETAILED DESCRIPTION OF THE PREFERRED EMBODIMENT

Figure 2:
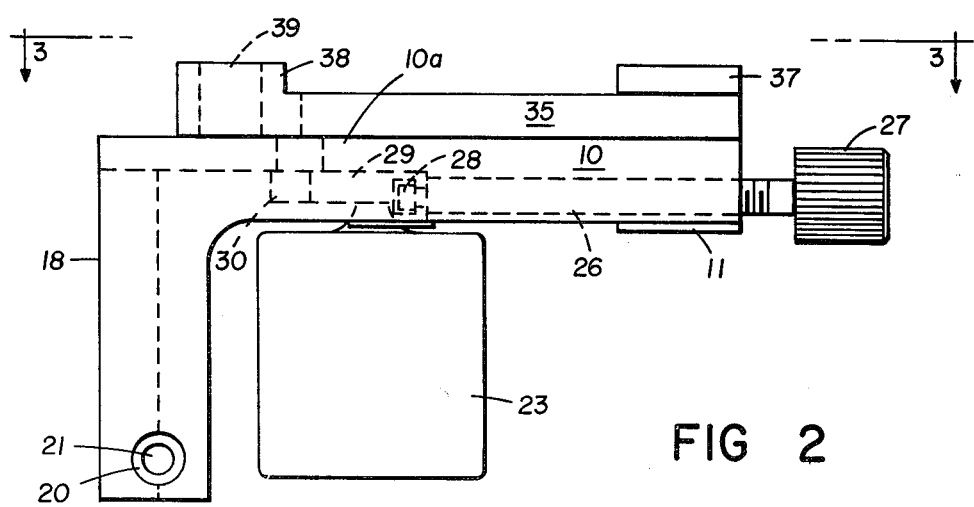
FIG. 2 is a side elevational view of the jig of FIG. 1.
Figure 6:
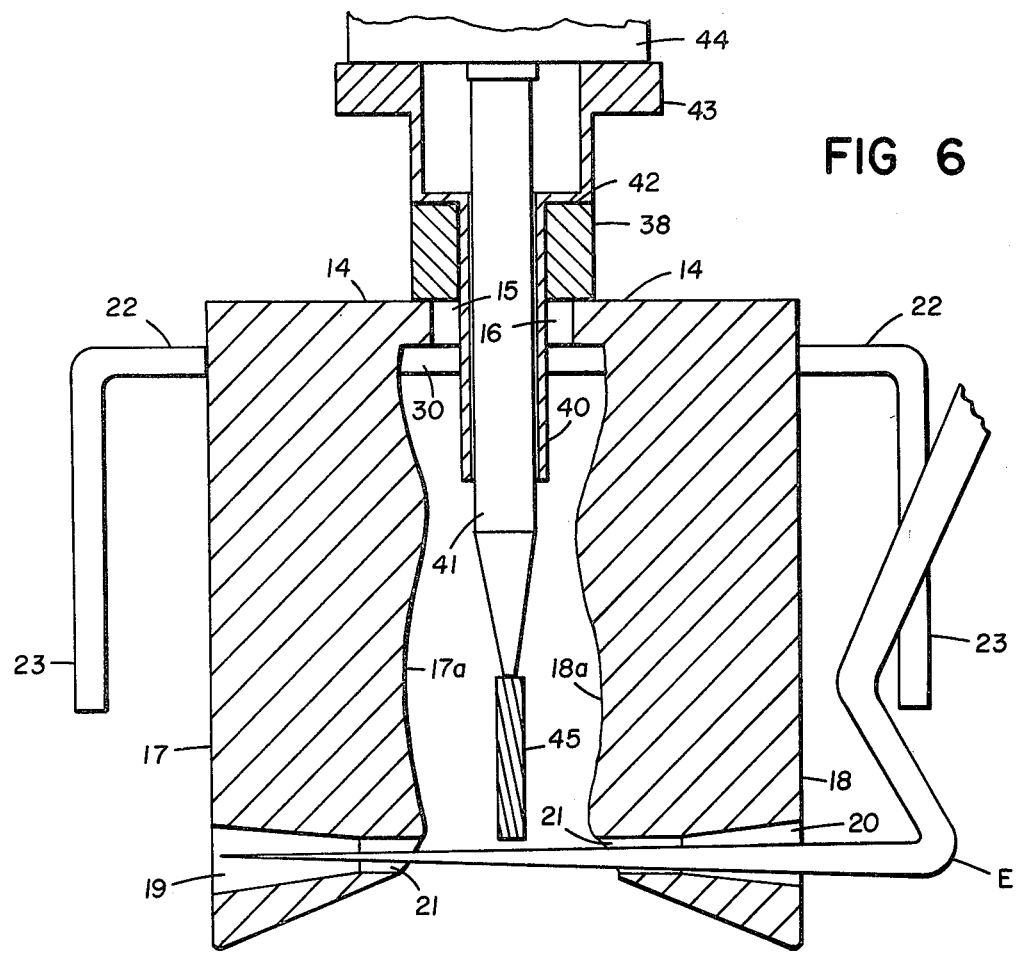
FIG. 6 is a sectional view taken along the line 6—6 of FIG. 3 and illustrating the cervical wall stop or guide and its setting, a dental hand-piece and burr being shown fitted with a cylindrical dental burr guide and positioned in the paralleling arm of the jig.

The basic jig comprises the guide table and paralleling arm, preferably of a suitable stainless steel as are the other parts of the jig. The guide table, generally referred to at 10, consists of a U-shaped spring member whose yoked or distal end includes an integral boss 11 extending inwardly axially of the table 10 midway between its legs 10a. The boss 11 is axially bored at 12, which bore is also carried through the adjacent yoked end of the table 10, and internally threaded; upstanding from the boss 11 is an integral pivot stub 13 whose upper end is externally threaded, all for purposes later described. The proximal ends of the legs 10a are provided with a pair of transverse, integral abutments 14 extending inwardly from the legs 10a to spacedly abut each other above the level of the bore 12. The opposing edges of the abutments 14 symmetrically diverge toward the adjacent proximal ends of the legs 10a to form buccal and lingual wall guide surfaces 15 and 16 normal to the top faces of the legs 10a and the abutments 14 which form a smooth table top face. Below the abutments 14 a pair of interproximal retentive arms 17 and 18 depend at generally right angles from the proximal ends of the legs 10a and integral therewith. The arms 17 and 18 are of generally pyramidal shape and cross-section and contoured as shown. Their apices 17a and 18a lie in a plane normal to the top face of the legs 10a and the abutments 14 in order to fit within and clamp against the opposite interproximal enbrasure areas between adjacent teeth and anchor the jig. The retentive arms 17 and 18 are horizontally bored through adjacent their lower ends to provide a pair of aligned cervical wall locators 19 and 20 which are internally waisted at 21, as best shown in FIGS. 2 and 6 and for purposes to be described.

Figure 1:
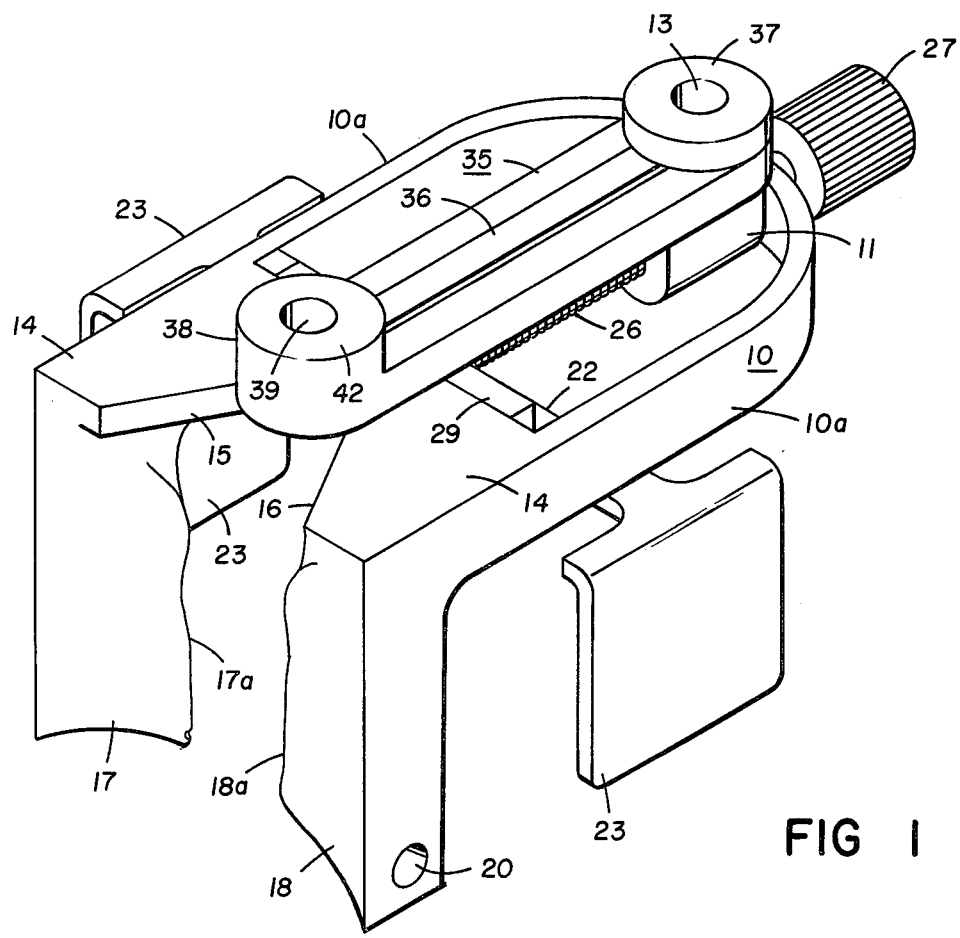
FIG. 1 is an upper isometric view of a jig according to the invention.

In order to assist application and removal of the jig, a pair of adjacent spreader arms 22 are provided. As best in FIGS. 1 and 3, the inner end of each arm 22 is secured to the inner face of one leg 10a inboard of the abutments 14. The arm 22 then passes across the table 10 along side the other arm 22 and emerges from under the latter outboard of the opposite leg 10a, the outer ends of the arms 22 being provided with down turned thumb and finger pressure tabs 23. Hence, squeezing the tabs 23 will spread the legs 10a and permit the retentive arms 17 and 18 to be applied to or released from the interproximal embrasure areas.

Figure 7:
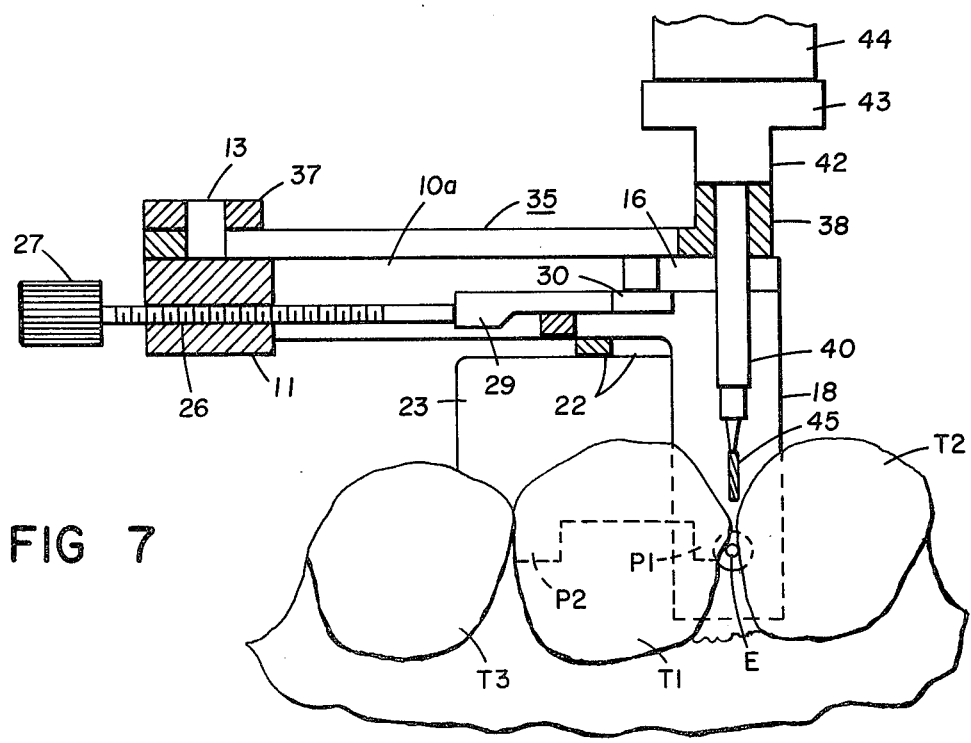
FIG. 7 is a sectional view taken along the lines 7—7 of FIG. 3, shown with the Jig, burr guide and hand-piece in position for cutting a proximal box.

As best shown in FIGS. 4 and 5, the axial wall guide, generally designated as 25, consists of a threaded shaft 26, fitted with a finger knob 27 at its outer end, which, as shown in FIG. 7 is threaded into the bore 12 of the boss 11. The inner end of the shaft 26 is socketed as shown at 28 in the rear edge of a spade-like plate 29 whose forward edge is convexly shaped to provide the axial wall guide surface 30, the plate 29 being disposed beneath the abutments 14 and riding on the spreader arms 22. Turning the knob 27 will thus move the plate 29, and hence the axial wall guide surface 30, axially of the guide table 10 between its legs 10a.

The paralleling arm itself, generally designated as 35, comprises a generally rectangular bar having an elongated vertical slot 36 therethrough. The width of the slot 36 accommodates the stub pivot 13 over which the arm 35 is placed and secured with a lock nut 37 so that the arm 35 can rotate about the pivot 13 and at the same time be slid back and forth relative to the latter owing to the slot 36. The arm 35 slides on and is supported by the top face of the table 10 for which purpose it will be noted from FIG. 3, that the width of the arm 35 is somewhat greater than the narrowest spacing between the abutments 14. The slot 36 terminates a distance from one end of the arm 35 whose upper face is integrally formed with an annular boss 38 whose bore 39 opens down through the arm 35. Fitting slidably within the boss 38 is the lower end of a dental burr guide in the form of a sleeve 40 which spacedly envelopes the burr chuck or collet 41. The upper end of the sleeve 40 is shouldered, so that the upper face of the boss 38 in effect forms a cervical wall guide surface 42, and terminates in a cup-like fitting 43 which screws onto the hand-piece or drill 44. The guide 40 thus prevents frictional engagement of the rotating burr 45 with the bore 39 and yet allows the latter to guide both vertical and horizontal movement of the burr 45 owing to the sleeve 40. If friction is not deemed a problem, the burr guide 40 can be omitted and the bore 39 made small enough to engage directly the rotating shank itself of the burr 45.

The use of the jig will be largely apparent to those skilled in the denstistry art. As indicated in FIGS. 6 and 7, the jig is applied by squeezing the tabs 23 to spread the interproximal retentive arms 17 and 18, placing the latter in the embrasure area between two adjacent teeth T1 and T2, and releasing the tabs 23, the jig then overlying the tooth T1 in preparation for the cutting of a proximal box P1 thereon. It will be observed that the spacing of the buccal and lingual wall guide surfaces 15 and 16 is determined by the spread of the retentive arms 17 and 18, and the latter in turn by the size of the teeth T1 and T2, so that the buccal and lingual walls of the box P1 are proportioned to the size of the teeth concerned. In this connection, the form of jig used for amalgam is preferably different from that used for cast gold in that the initial spacing of the buccal and lingual wall guide surfaces 15 and 16 is narrower in the case of the former than it is in the case of the latter in order to reflect the typical difference in the spacing between the buccal and lingual walls of the boxes for these two preparation.

Preferably the location of the axial wall of the box P1 is set beforehand from a radiograph by adjustment of the axial wall guide 25 by the knob 27. Once the jig is in position, the location of the cervical wall of the box P1 can be found by locating the cervical embrasure with a right angle explorer E (see FIGS. 6 and 7) inserted through the cervical wall locators 19 and 20 and adjusting the position of the retentive arms 17 and 18 as necessary. Then the proper burr 45, calibrated for length, is inserted in the hand-piece 44 and adjusted so that it protrudes from the latter the distance (which is fixed and known) between the locators 19 and 20 and the cervical wall guide surface 42. Thereafter, the box P1 can be quickly and accurately cut by inserting the burr guide 40 into the bore 39 and manupulating the paralleling arm 35 about its pivot 13 and along its slot 36. Note that preferably the overall length of the arm 35 when fully extended from the pivot 13 is such that the burr 45 does not operate beyond a plane through the apices 17a and 18a of the retentive arms 17 and 18, i.e., the arc of the burr is no more than tangent to a plane through the cervical embrasure between the teeth T1 and T2 so as not to cut or damage the adjacent tooth T2. If a second proximal box P2 opposite the box P1 is also to be cut on the tooth T1, as for a MOD, inlay or onlay, the jig is removed, rotated 180° and the retentive arms 17 and 18 similarly positioned in the embrasure area between the teeth T1 and T3. In order to insure that the buccal, lingual, axial and cervical walls of the box P2 are parallel to those of the box P1, so that the casting will fit properly, the paralleling arm 35 is swung around on its pivot 13 and in the slot 36 until the burr guide 40 is over the box P1. The burr can then be inserted and held against the buccal, lingual and axial walls of the box P1 while the position of the retentive arms 17 and 18 between the teeth T1 and T3 is adjusted to insure that when the paralleling arm 35 is swung back into cutting position for the box P2, the walls of the latter will be parallel to those of the box P1.

Though the axial and cervical wall guide surfaces 30 and 42 are preferable, they are not as essential to the jig as are the buccal and lingual wall guide surfaces 15 and 16, the retentive arms 17 and 18, and the paralleling arm 35, so that conceivably one or both could be omitted. Nor is it mandatory that the axial wall guide 25 (if present) be adjustable, though that also is preferable. Instead, it could be fixed. Furthermore, the cervical wall guide surface 42 could also be made adjustable relative to the guide table 10, though this is not deemed really necessary. In any event, though the invention has been described in terms of a particular embodiment, being the best mode known of carrying out the invention, it is not limited to that embodiment alone. Instead, the following claims are to be read as encompassing all adaptations and modifications of the invention falling within its scope and spirit.

I claim:

1. A jig for the cutting of proximal boxes in dentistry comprising: a guide table having a pair of spaced interproximal retentive arms extending in one transverse direction from the guide table, the retentive arms having opposed embrasure portions effective to engage the opposite embrasure areas between adjacent teeth, the spacing between the retentive arms being variable in order for the embrasure portion to clampingly engage said embrasure areas in order to support the guide table in overlying relation to a tooth to be provided with a proximal box, the guide table having spaced opposed buccal and lingual wall guide surfaces disposed transversely of the guide table; and a paralleling member mounted to the guide table for paralleling movement over the guide table in a plurality of directions, the paralleling member including dental burr holding means adapted to receive and dispose a dental burr transversely of the guide table for movement between the buccal and lingual wall guide surfaces during said movement of the paralleling member in order to determine the location of the buccal and lingual walls of a proximal box.

2. The jig of claim 1 wherein the guide table includes an axial wall guide surface disposed transversely of and between the buccal and lingual wall guide surfaces, the axial wall guide surface being effective to guide a dental burr in the burr holding means during said movement of the paralleling member in order to determine the location of the axial wall of a proximal box.

3. The jig of claim 1 wherein the dental burr holding means permits reciprocal movement of the dental burr in opposite directions transversely of the guide table, and wherein the guide table includes a cervical wall guide surface in spaced relation to the guide table effective to limit movement of a dental burr in the burr holding means in one of said opposite transverse directions during said movement of the paralleling member in order to determine the location of the cervical wall of a proximal box.

4. The jig of claim 1 wherein the guide table includes an axial wall guide surface disposed transversely of and between the buccal and lingual wall guide surfaces, the axial wall guide surface being effective to guide a dental burr in the burr holding means during said movement of the paralleling member in order to determine the location of the axial wall of a proximal box; and wherein the dental burr holding means permits reciprocal movement of the dental burr in opposite directions transversely of the guide table, and including a cervical wall guide surface in spaced relation to the guide table effective to limit movement of a dental burr in the burr holding means in one of said opposite transverse directions during said movement of the paralleling member in order to determine the location of the cervical wall of a proximal box.

5. The jig of claim 4 including an axial wall guide member providing the axial wall guide surface and adjustably movable relative to the guide table in opposite directions substantially parallel to the guide table.

6. The jig of any of claims 1, 2, 3, 4 or 5 in which increasing or decreasing of the spacing between the embrasure portions of the retentive arms at the same time respectively increases or decreases the spacing between the buccal and lingual wall guide surfaces.

7. The jig of claim 1 wherein the guide table comprises a generally U-shaped member of resilient material, one side of the arms and yoke of the table member having a common face in a first plane constituting a table guide face, the arms of the table member adjacent their open ends having a pair of spaced integral legs extending tranversely from the other side of the arms and yoke of the table member, the legs constituting the interproximal retentive arms and providing said opposed embrasure portions, the embrasure portions being generally pyramidal in cross-section with opposed apices in a second plane normal to said first plane of the table guide face, said ends of the table member arms adjacent their juncture with the retentive arms being formed to provide a pair of spaced opposed surfaces normal to the table guide face, said surfaces also diverging outwardly toward said table member arm ends and constituting the buccal and lingual wall guide surfaces; a paralleling arm slidably disposed on the table guide face; a pivot carried by the table member at a location remote from said table member arm ends and pivotally engaging one end of the paralleling arm about an axis normal to the table guide face, the paralleling arm having a longitudinal slot slidably engaging said pivot, said pivot and slot together being effective so that the paralleling arm is both slidable along and swingable about said pivot while in slidable contact with the table guide face; and dental burr locating means carried by the other end of the paralleling arm for receiving and holding a dental burr in a position normal to the table guide face and between the buccal and lingual wall surfaces, the paralleling arm having a length such that when said pivot is engaged with said one paralleling arm end and a dental burr is received in and held by the burr locating means, the burr is swingable by the paralleling arm between the buccal and lingual guide surfaces in an arc substantially tangent to said second plane.

8. The jig of claim 7 including a convex axial wall guide surface carried by the guide table member and disposed normal to the table guide face between the buccal and lingual wall guide surfaces.

9. The jig of claim 8 wherein the burr holding means allows reciprocal movement of the burr in opposite directions normal to the table guide face and including a cervical wall guide surface limiting movement of the burr in one of said directions.

10. The jig of claim 9 including an axial wall guide member supported on the guide table member for reciprocal movement along a path between the buccal and lingual wall guide surfaces and the axis of said pivot, the axial wall guide member having a surface thereon constituting the axial wall guide surface, and means for adjusting the position of the axial wall guide member along said path.

* * * * *